United States Patent [19]

Bull et al.

[11] Patent Number: 5,639,888

[45] Date of Patent: Jun. 17, 1997

[54] PROCESS FOR THE PREPARATION OF ACID CHLORIDE COMPOUNDS

[75] Inventors: Michael John Bull, Sittingbourne; John Warcup Cornforth, Lewes, both of England

[73] Assignee: American Cyanamid Co., Madison, N.J.

[21] Appl. No.: 317,260

[22] Filed: Oct. 3, 1994

[51] Int. Cl.$^6$ .......................... C07D 213/46; C07C 53/44; C07C 53/46

[52] U.S. Cl. .......................... 546/314; 546/315; 562/840

[58] Field of Search .......................... 562/840; 546/314, 546/315

[56] References Cited

U.S. PATENT DOCUMENTS

| | | | |
|---|---|---|---|
| 3,875,226 | 4/1975 | Doorenbos et al. | 562/851 |
| 4,560,794 | 12/1985 | Foster | 562/467 |
| 4,562,286 | 12/1985 | Foster | 562/467 |
| 5,064,959 | 11/1991 | Pawlowski et al. | 544/216 |
| 5,068,343 | 11/1991 | Beck et al. | 548/194 |
| 5,072,038 | 12/1991 | Klauke et al. | 562/840 |

OTHER PUBLICATIONS

Nakano, T. et al., "Convenient Synthesis of Aromatic Acid Chlorides. The Reaction of Benzylidyne Chlorides with Hexamethyldisiloxane", *J.C.S. Chem. Comm.*, pp. 808–809 (1977).

Hill, Marion E., "Metal Halide Catalyzed Hydroylsis of Trichloromethyl Compounds", *J. Org. Chem.*, pp. 1115–1117 (1960).

*Primary Examiner*—Alan L. Rotman
*Attorney, Agent, or Firm*—Gregory M. Hill

[57] ABSTRACT

A process for preparing a compound of general formula

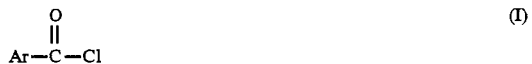

where Ar represents an optionally substituted aromatic or heteroaromatic group, the process comprising reacting a compound of general formula

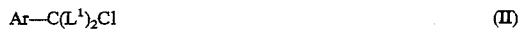

where each $L^1$ independently represents a leaving group (preferably a chlorine atom), with water in the presence of a Lewis acid and a chlorocarbon solvent which includes at least two chlorine atoms, is disclosed.

6 Claims, No Drawings

PROCESS FOR THE PREPARATION OF ACID CHLORIDE COMPOUNDS

This invention relates to a process for the preparation of acid chloride compounds.

J.C.S. Chem. Comm (1977), 808–9 discloses a process for preparing aromatic acid chlorides. The process involves reacting substituted benzylidyne chlorides with hexamethyldisiloxane in the presence of iron (III) chloride to produce the corresponding substituted benzoyl chloride. In the reaction, trimethylchlorosilane is produced which must be hydrolysed back to hexamethyldisiloxane for re-use.

J.O.C. (1960), 115–7 discloses a process of metal halide catalysed hydrolysis of trichloromethyl compounds to form acids. For example, the document discloses that (trichloromethyl)benzene may be reacted with water in the presence of ferric chloride and chloroform as a solvent to produce benzoic acid.

This invention is based upon the discovery of a novel process for preparing acid chloride compounds.

According to a first aspect of the present invention, there is provided a process for preparing a compound of general formula

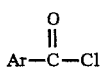

(I)

where Ar represents an optionally substituted aromatic or heteroaromatic group, the process comprising reacting a compound of general formula

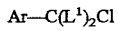

(II)

where each $L^1$ independently represents a leaving group, with water in the presence of a Lewis acid and a chlorocarbon solvent which includes at least two chlorine atoms.

It is believed that the two chlorine atoms of the chlorocarbon solvent may form a transition state or intermediate in the reaction which aids the preferential formation of the desired acid chloride of general formula I.

Preferably, each $L^1$ independently represents a halogen atom. Preferred halogen atoms are chlorine, bromine and iodine atoms. Preferably, both of said groups $L^1$ represent a chlorine atom.

Said Lewis acid is preferably a weak Lewis acid. Said Lewis acid is preferably a halide of a transition metal. Preferably, said Lewis acid is a chloride of a transition metal. Preferred transition metals include iron, gallium and antimony. Preferred Lewis acids include $FeCl_3$, $GaCl_3$ and $SbCl_5$. Most preferably, the Lewis acid is ferric chloride ($FeCl_3$).

Said Lewis acid, for example ferric chloride, is preferably substantially anhydrous.

Preferably, a catalytic amount of said Lewis acid is added in said process. For example, the molar ratio of said Lewis acid to said compound of general formula II is preferably less than 0.15 and, more preferably, is less than 0.1.

Said chlorocarbon solvent preferably includes at least two carbon atoms. Preferably, a respective said chlorine atom is bonded to each of said at least two carbon atoms. Said chlorocarbon solvent preferably includes a respective chlorine atom bonded to each of two adjacent carbon atoms.

Said chlorocarbon solvent is preferably of general formula

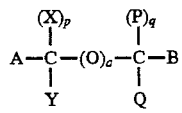

(III)

where at least two of A, B, X, Y, P and Q represent a chlorine atom and where each of the others is independently selected from a hydrogen or halogen (especially chlorine) atom, or an optionally substituted alkyl or alkenyl group; a=0 or 1; p=q=0 or 1; provided that where a=1, p=q=1.

Preferably, a=0 in said solvent of general formula III. Preferably at least two of A, B, X, Y, P and Q represent a chlorine atom and the others independently represent a hydrogen or chlorine atom or an optionally substituted, preferably unsubstituted, $C_{1-4}$ alkyl group.

Preferably, water is of low solubility in said chlorocarbon solvent. In view of this, Dean and Stark apparatus may be used to deliver water slowly in to the reaction mixture. Suitable chlorocarbon solvents have a solubility of less than 0.30 g/100 g water at 25° C. and, more preferably, have a solubility of less than 0.20 g/100 g at 25° C.

Preferably, said chlorocarbon solvent is 1,2-dichloroethane. This solvent has a solubility of 0.15 g/100 g water at 25° C. (Techniques of Organic Chemistry, vol. VII, Organic Solvents). Dichloroethane has been found to be a surprisingly advantageous solvent for use in the preferential formation of the desired acid chloride of general formula I.

Preferably, in the process of the first aspect, approximately equimolar amounts of the compound of general formula II and water are reacted together. Preferably, in the process, the compound of general formula II and the Lewis acid are mixed together in said chlorocarbon solvent, suitably at an elevated temperature, preferably under reflux. Said water is preferably added to the mixture over an extended period of time. During the addition, the reaction mixture is preferably refluxed. Said water is preferably added to the reaction mixture so that all added water dissolves in the reaction mixtures. Dean and Stark apparatus is of utility in achieving this aim. With Dean and Stark apparatus, water is dissolved in the chlorocarbon solvent of the reaction mixture so that the chlorocarbon solvent is saturated with water.

After the added water has reacted with the compound of general formula II, the Lewis acid may be removed from the mixture, for example, by filtration.

The compound of general formula I may be isolated by standard techniques. Alternatively, the compound of general formula I in the reaction mixture may be further reacted. For example, the process of the first aspect may be of utility in the preparation of herbicidal carboxamide derivatives described in European Patent Application No. 0 447 004 (Shell), the contents of which are incorporated herein by reference. In this case, preferably the group Ar in said compound of general formula I represents an optionally substituted heteroaromatic group. Preferably, said optionally substituted heteroaromatic group is an optionally substituted pyridyl group of general formula

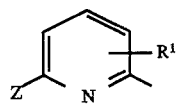

(IV)

where $R^1$ represents a hydrogen or halogen atom or an alkyl or haloalkyl group and Z represents a halogen atom. Preferably, in said pyridyl group of general formula IV, Z represents a chlorine atom and $R^1$ represents a hydrogen atom.

Preferably, the further reaction of said compound of general formula I involves reacting the compound of general formula I with a compound of general formula

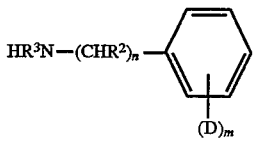

where $R^2$ represents a hydrogen atom or an alkyl group; $R^3$ represents a hydrogen atom or an alkyl or alkenyl group; the or each group D independently represents a halogen atom or an alkyl, nitro, cyano, haloalkyl, alkoxy or haloalkoxy group; n represents 0 or 1; and m represents 0 or an integer from 1 to 5, to prepare a compound of general formula

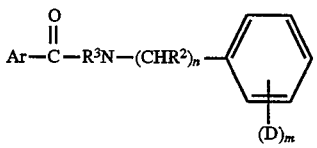

Preferably, in said compound of general formula VI, $R^3$ represents a hydrogen atom, m represents 1, D represents a fluorine atom in the 4-position relative to the amine group, and n represents 0.

Said compound of general formula VI may be further reacted to prepare compounds of general formula

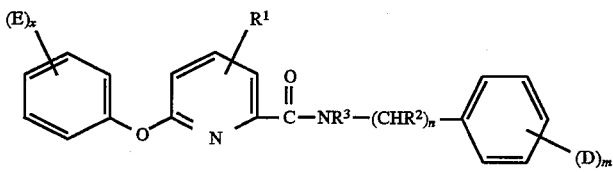

where $R^1$, $R^2$, $R^3$, D, n and m are as described in any statement herein, each group E independently represents a halogen atom or an optionally substituted alkyl, alkoxy, alkenyloxy, alkynyloxy, cyano, carboxy, alkoxycarbonyl, alkylthiocarbonyl, alkylcarbonyl, amide, alkylamido, nitro, alkylthio, haloalkylthio, alkenylthio, alkynylthio, alkylsulphinyl, alkylsulphonyl, alkyloximinoalkyl or alkenyloximinoalkyl group, and x represents 0 or an integer from 1 to 5.

According to a second aspect of the invention, there is provided a process for preparing a compound of general formula VI, the process including the process step of said first aspect.

According to a third aspect of the invention, there is provided a process for preparing a compound of general formula VII, the process including the process step of said first aspect.

The invention extends to a compound of general formula I, when prepared by the process of the first aspect.

The invention extends to a compound of general formula VI when prepared using the process of the second aspect.

The invention extends to a compound of general formula VII when prepared using the process of the third aspect.

The invention will now be further described, with reference to the following Examples.

Examples 1 and 4 describe the preparation of certain acid chloride compounds. Examples 2, 3 and 5 describe subsequent reactions of the acid chloride compounds.

EXAMPLE 1

Preparation of 2-chloro-6-pyridinecarbonyl chloride [Ar=2-chloro-6-pyridyl in the compound of general formula I]

Nitrapyrin [2-chloro-6-(trichloromethyl)pyridine; Ar=2-chloro-6-pyridyl and $L^1=L^2=Cl$ in the compound of general formula II] (46.2 g; 0.2M), 1,2-dichloroethane (1 liter) and anhydrous ferric chloride ($FeCl_3$) (8.1 g; 0.04M) were stirred under reflux for half-an-hour using a Dean and Stark separator. Water (3.6 g) was then added to the Dean and Stark separator and the reaction mixture was stirred under reflux for 24 hours, by which time all the water had been consumed. Gas-liquid chromatography showed 93% product on the treatment with 4-fluoroaniline (see Example 2). The ferric chloride was then filtered off and the filtrate concentrated.

EXAMPLE 2

Preparation of N-(4-fluorophenyl)-2-chloro-6-pyridinecarboxamide

To the concentrated filtrate of Example 1 was added 4-fluoroaniline (28 g; 0.25M) at 20°–70° C. The mixture was then stirred under reflux for ¾ hr, by which time gas evolution had ceased. The mixture was then cooled to 20° C., washed with dilute hydrochloric acid and stripped to give a reddish brown oil (50.5 g) which was then dissolved in dichloromethane and passed through a $SiO_2$ pad to give the desired product (37.3 g; yield 74% based on Nitrapyrin added). Gas-liquid chromatography showed 99% pure.

EXAMPLE 3

Preparation of N-(fluorophenyl)-2-(3-α,α,α-trifluoromethyl phenoxy)-6-pyridinecarboxamide To a slurry of potassium carbonate (435 g; 3.15 moles) in dimethylformamide (1.8 liters) was added the pyridinecarboxamide of Example 2 (752 g; 3.0 moles) and 3-trifluoromethylphenol (502 g; 3.1 moles) and the mixture brought to reflux under nitrogen for 5 hours. Evolution of carbon dioxide began at ca. 120° C. After cooling, the reaction mixture was added to 0.6M hydrochloric acid (10.5 liters) and extracted with methylene chloride (2×2.5 liters). The organic extracts were combined and back-washed with water (10 liters) and the solvent flashed. The residue, after decolouration through a short column of silica gel, was recrystallised from cyclohexane/isopropanol (1:3; 4.7 liters) to give the title compound (835 g; 74% yield) mp. 105°–107° C. cyclohexane/isopropanol (1:3; 4.7 liters) to give the title compound (835 g; 74% yield) top. 105°–107° C.

EXAMPLE 4

Preparation of Benzoyl Chloride

α, α,α-Trichlorotoluene (19.6 g; 0.1M), ferric chloride (4.1 g; 0.02M) and 1,2-dichloroethane (500 ml) were stirred under reflux under heavier than water Dean and Stark apparatus. Water (1.8 g) was then added to the Dean and Stark apparatus and the mixture was refluxed for 4 hours. By this time, all of the water had been consumed. The mixture was then filtered through Hyflo (Trade Mark) to remove the ferric chloride.

EXAMPLE 5

Preparation of N-(4-fluorophenyl) phenylcarboxamide

To the filtrate of Example 4 was added 4-fluoroaniline (22.2 g; 0.22M) with stirring over 15 minutes. Dilute hydrochloric acid was then added, the organic layer separated and the remainder was stripped to give a dark red solid (25 g). The solid was dissolved in dichloromethane and passed through a $SiO_2$ pad to give the title compound (6.3 g; 29% yield).

We claim:

1. A process for preparing a compound of general formula

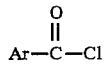   (I)

where Ar represents, a pyridyl group of general formula

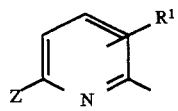   (IV)

where $R^1$ represents a hydrogen or halogen atom or an alkyl or haloalkyl group and Z represents a halogen atom, the process comprising reacting a compound of general formula $$Ar\text{—}C(L^1)_2Cl \quad \text{(II)}$$

where each $L^1$ independently represents a leaving group, with water in the presence of a Lewis acid and a chlorocarbon solvent which includes at least two chlorine atoms.

2. The process according to claim 1, where each $L^1$ independently represents a halogen atom.

3. The process according to claim 2 where both of said groups $L^1$ represent a chlorine atom.

4. The process according to claim 1 where the Lewis acid is ferric chloride.

5. The process according to claim 1 where said chlorocarbon solvent is of general formula

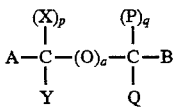   (III)

where at least two of A, B, X, Y, P and Q represent a chlorine atom and where each of the others is independently selected from a hydrogen or halogen atom, or an optionally substituted alkyl or alkenyl group; and a=0 or 1; p=q=0 or 1; provided that where a=1, p=q=1.

6. The process according to claim 1 where said chlorocarbon solvent is dichloroethane.

* * * * *